United States Patent
Erkens et al.

(10) Patent No.: US 10,342,751 B2
(45) Date of Patent: Jul. 9, 2019

(54) DOUBLE-CHAMBER POUCH FOR DYEING HUMAN HAIR

(71) Applicant: Henkel AG & Co. KGaA, Duesseldorf (DE)

(72) Inventors: Udo Erkens, Willich (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 83 days.

(21) Appl. No.: 15/729,743

(22) Filed: Oct. 11, 2017

(65) Prior Publication Data

US 2018/0098927 A1    Apr. 12, 2018

(30) Foreign Application Priority Data

Oct. 12, 2016   (DE) .................. 10 2016 219 860

(51) Int. Cl.

| | |
|---|---|
| *A61Q 5/10* | (2006.01) |
| *A61K 8/41* | (2006.01) |
| *A61K 8/19* | (2006.01) |
| *A61K 8/20* | (2006.01) |
| *A61K 8/22* | (2006.01) |
| *A61K 8/25* | (2006.01) |
| *A61K 8/34* | (2006.01) |
| *A61K 8/81* | (2006.01) |
| *A61K 8/42* | (2006.01) |

(52) U.S. Cl.
CPC ............... *A61K 8/411* (2013.01); *A61K 8/19* (2013.01); *A61K 8/20* (2013.01); *A61K 8/22* (2013.01); *A61K 8/25* (2013.01); *A61K 8/347* (2013.01); *A61K 8/415* (2013.01); *A61K 8/42* (2013.01); *A61K 8/8147* (2013.01); *A61Q 5/10* (2013.01); *A61K 2800/4324* (2013.01); *A61K 2800/882* (2013.01)

(58) Field of Classification Search
CPC ............... A61Q 5/10; A61K 2800/882; A61K 2800/4324; A61K 8/19; A61K 8/411; A61K 2800/88; A61K 8/25; A61K 8/8147; A61K 8/347; A61K 8/415
See application file for complete search history.

(56) References Cited

U.S. PATENT DOCUMENTS

| | | | |
|---|---|---|---|
| 4,156,047 A | 5/1979 | Wysong | |
| 10,179,093 B2 * | 1/2019 | Erkens | ................. A61Q 5/08 |
| 2017/0312188 A1 | 11/2017 | Erkens et al. | |

FOREIGN PATENT DOCUMENTS

| | | |
|---|---|---|
| DE | 4436863 C1 | 1/1996 |
| DE | 4436862 C1 | 2/1996 |
| GB | 1330745 A | 9/1973 |
| WO | 02060980 A2 | 8/2002 |
| WO | 03089330 A1 | 10/2003 |
| WO | 2016074853 A1 | 5/2016 |
| WO | WO2016/074853 A1 * 5/2016 ............... A61Q 5/10 |
| WO | 2016207347 A1 | 12/2016 |

OTHER PUBLICATIONS

Intellectual Property Office, Search Report under Section 17(5) for United Kingdom Patent Application No. GB1716622A dated Jun. 29, 2018.

* cited by examiner

Primary Examiner — Eisa B Elhilo
(74) Attorney, Agent, or Firm — Lorenz & Kopf, LLP

(57) ABSTRACT

The present disclosure relates to a cosmetic product for dyeing keratin fibres which contains two separate powdered preparations (A) and (B), which are each packaged in a water-soluble film, and to a method for dyeing keratin fibres using said product. The cosmetic product of the present disclosure does not require the use of free hydrogen peroxide.

20 Claims, No Drawings

DOUBLE-CHAMBER POUCH FOR DYEING HUMAN HAIR

CROSS-REFERENCE TO RELATED APPLICATION

This application claims priority to German Patent Application No. 10 2016 219 860.2, filed Oct. 12, 2016, which is incorporated herein by reference in its entirety.

TECHNICAL FIELD

The present disclosure relates to a cosmetic product for dyeing keratin fibres which contains two separate solid preparations (A) and (B), which are each packaged in a water-soluble film, and to a method for dyeing keratin fibres using said product.

BACKGROUND

In order to provide colour-changing cosmetic products, in particular for keratin fibres, such as hair for example, a person skilled in the art is aware of various dye systems depending on the demands placed on the colouring. For permanent, intense colouring with corresponding fastness properties, what are known as oxidation dyes are used, which are generally provided in two parts. Here, an alkaline preparation of what are known as oxidation dye precursors (ODPs) is used as first part and contains what are known as developer components and coupler components, which form the actual dyes with one another under the influence of oxidising agents, such as hydrogen peroxide. The oxidising agent preparation, as second part, which is often also referred to as a developer, contains at least water and hydrogen peroxide and is set to an acidic pH for stability reasons.

The oxidising agent preparation set to an acidic pH is mixed with the alkaline part, which is set to an alkaline pH just before use, usually in a ratio by weight of first part (set to an alkaline pH) to oxidising agent preparation of from about 1:1 to about 1:2. This mixture for use is applied to the hair, left there usually for approximately 30 to 45 minutes, and is then rinsed out. During this time, the oxidation dye precursors (ODPs) react with one another under the influence of the hydrogen peroxide to form oligomers, wherein the desired hair colour develops.

Conventional colorants consist of a liquid oxidising agent and a colour cream.

Document WO 03/089330 A1 discloses a permanent hair dye composition in which the developer and oxidising agent dye constituents are disposed in a flexible two-chamber container, which allows both dye constituents to be pushed out using the fingers.

DE 4436863 C1 and DE 4436862 describe two-chamber containers for hair colorants which enable the dye constituents to be dosed by a mechanical closure system. The containers described in these documents have the disadvantage that, at the end, a container remains which has to be disposed of. Furthermore, the use of hydrogen peroxide as oxidising agent is described in both documents, however this, as liquid component, if handled incorrectly, for example if it comes into contact with the skin or eyes, can lead to irritations or in extreme cases can even trigger allergies.

Document WO 2016/074853 A1 discloses a cosmetic product for dyeing keratin fibres, in which one of the components is packaged in a water-soluble film and the other component is again an aqueous oxidising agent solution.

BRIEF SUMMARY

An exemplary cosmetic product for dyeing keratin fibers is provided and comprises a preparation (A) and a preparation (B), wherein preparations (A) and (B) are packaged separately from one another and wherein the preparations (A) and (B) are packaged in a water-soluble film. Preparation (A) comprises (a) at least one colorant from the group of oxidation dye precursors and substantive dyes, and (b) hydrated sodium silicate in an amount of from about 20 to about 80 wt. %, in relation to the total weight of preparation (A). Preparation (B), in relation to its total weight, comprises at least one member from the group of percarbamide, percarbonates and perborates, in a total amount of from about 0.5 to about 95 wt. %.

An exemplary method for dyeing keratin fibers is provided. The method includes preparing a preparation (A) comprising, based on its total weight, (a) at least one colorant from the group of oxidation dye precursors and substantive dyes, and (b) hydrated sodium silicate in an amount of from about 20 to about 80 wt. %. Further, the method includes preparing a preparation (B) comprising, based on its total weight, at least one member from the group of percarbamide, percarbonates and perborates, in a total amount of from about 0.5 to about 95 wt. %. The method includes packaging the preparations (A) and (B) separately from one another in a water-soluble film as a cosmetic agent and adding the cosmetic agent to water in order to dissolve the water-soluble film to form an application mixture. The volume ratio of the totality of the preparations (A) and (B) to the water is from about 1:2 to about 1:8. The method includes treating the keratin fibers with the application mixture.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is to provide a colorant with which there is no risk of overdosing, with which there is less waste to be disposed of, and with which a liquid hydrogen solution is no longer necessary. Nevertheless, the colorant should have excellent colouring properties.

It has now surprisingly been found that this can be achieved by a cosmetic product for dyeing keratin fibres in which both constituents are present in powdered or solid form, wherein both constituents are packaged separately from one another in a water-soluble film, and both constituents contain defined ingredients.

The present disclosure relates to:
1. A cosmetic product for dyeing keratin fibres, containing at least two preparations (A) and (B) packaged separately from one another, wherein
the preparation (A) contains
(a) at least one colorant from the group of oxidation dye precursors and substantive dyes and (b) hydrated sodium silicate in an amount of from about 20 to about 80 wt. %, in relation to the total weight of preparation (A), the preparation (B), in relation to its total weight, contains at least one member from the group of percarbamide, percarbonates and perborates, in a total amount of from about 0.5 to about 95 wt. %, and the preparations (A) and (B) are packaged in a water-soluble film.

2. The product according to point 1, wherein the product is produced as a two-chamber bag (pouch) containing the preparations (A) and (B) in the two chambers.
3. The product according to either one of the preceding points, wherein the hydrated sodium silicate (b) has a molar ratio $Na_2O:SiO_2$ of from about 1:2 to about 1:3.
4. The product according to any one of the preceding points, wherein the hydrated sodium silicate (b) has a molar ratio $Na_2O:SiO_2$ of from about 1:2.5 to about 1:2.8.
5. The product according to any one of the preceding points, wherein the preparation (A), as colorant, contains p-toluylenediamine or a physiologically acceptable salt thereof in an amount of from about 0.5 to about 30 wt. %, resorcinol in an amount of from about 0.3 to about 18 wt. %, and m-aminophenol in an amount of from about 0.3 to about 6.0 wt. %, in each case in relation to the total amount of the preparation (A).
6. The product according to any one of the preceding points, wherein the preparation (A) and/or the preparation (B) also contains a filler, such as magnesium carbonate.
7. The product according to any one of the preceding claims, wherein the preparation (A) contains, in relation to its total weight, p-toluylenediamine disulfate in an amount of from about 5 to about 15 wt. %, resorcinol in an amount of from about 3 to about 10 wt. %, m-aminophenol in an amount of from about 1.5 to about 3.0 wt. %, and the hydrated sodium silicate (b) in an amount of from about 20 to about 80 wt. %.
8. The product according to any one of the preceding points, wherein the preparation (B) contains the percarbamide, percarbonate and/or perborate in a total amount of from about 25 to about 95 wt. %, in relation to its total weight.
9. The product according to any one of the preceding points, wherein the water-soluble film, in relation to its total weight, consists to an extent of at least 60 wt. % of a polymer mixture having a multimodal molecular weight distribution.
10. The product according to point 9, wherein the polymer mixture, in relation to its total weight, consists to an extent of at least 60 wt. %, such as to an extent of at least 80 wt. %, for example to an extent of at least 90 wt. %, and such as to an extent of at least 95 wt. % of a mixture comprising a1) water-soluble vinyl alcohol/vinyl acetate copolymer a1) and a2) at least one water-soluble vinyl alcohol/vinyl acetate copolymer a2) different from the water-soluble vinyl alcohol/vinyl acetate copolymer a1), or of a mixture comprising a1) water-soluble vinyl alcohol/vinyl acetate copolymer a1) and a2) at least one, possibly modified water-soluble polysaccharide, such as at least one water-soluble polysaccharide from the group of methylcellulose, carboxymethylcellulose, ethyl cellulose, hydroxyethyl cellulose, hydroxypropyl cellulose, hydroxypropyl methylcellulose, dextrin and hydroxypropyl starch, for example at least one water-soluble polysaccharide from the group of hydroxypropyl starches.

11. The product according to any one of the preceding points, wherein the ratio by weight of the preparation (A) to the preparation (B) is from about 10:1 to about 1:10, such as from about 5:1 to about 1:5, for example from about 3:1 to about 1:3.
12. The product according to any one of the preceding points, in which the preparations (A) and (B) are present in the form of a powder.
13. The product according to any one of the preceding points, in which the preparation (B) contains only percarbamide as oxidising agent.
14. A method for dyeing keratin fibres using the cosmetic product according to any one of the preceding claims, in which at least one mixture for use is prepared from the preparations (A) and (B) packaged separately from one another by placing the preparations (A) and (B) packaged in a water-soluble film in water in order to dissolve the water-soluble films, wherein the volume ratio of the totality of preparations (A) and (B) to the water is from about 1:2 to about 1:8, such as from about 1:2 to about 1:3, and then treating keratin fibres with the mixture for use.
15. The method according to point 14, wherein the preparations (A) and (B) are packaged connected to one another in a two-chamber bag (pouch), and the two-chamber bag is placed in the water in order to produce the mixture for use.

Due to the contained hydrated sodium silicate in preparation (A) and the oxidising agent in preparation (B) in the specified amount ranges, it could be ensured surprisingly that, once the water-soluble films have dissolved and the preparations (A) and (B) have mixed, an effective dye mixture for use is produced, without the need to use hydrogen peroxide.

In principle, all animal hair, for example wool, horsehair, angora hair, fur, feathers and products or textile is produced therefrom, can be used as keratin-containing fibres. However, embodiments herein are used for the treatment of human hair and wigs manufactured therefrom.

Besides the oxidation dye precursors and/or substantive dyes, an essential constituent of the preparation (A) is (a) the hydrated sodium silicate. This is a sodium silicate soluble in water with a molar ratio $Na_2O:SiO_2$ of from about 1:2 to about 1:3, such as from about 1:2.5 to about 1:2.8. A hydrated sodium silicate that is particularly suitable as contemplated herein is commercially available under the name Britesil® 265 (PQ Corporation). The hydrated sodium silicate acts as an alkalising agent. The preparation (A) contains the hydrated sodium silicate in an amount of from about 20 to about 80 wt. %, such as from about 25 to about 78 wt. %, for example from about 30 to about 76 or from about 35 to about 75 wt. %, in relation to the total weight of the preparation (A).

As colorant (a), the preparation (A) contains oxidation dye precursors and/or substantive dyes.

In a first exemplary embodiment the preparation (A) contains at least one oxidative colorant (oxidation dye precursor). Oxidative colorants are understood as contemplated herein to be products which change the colour of hair and which cause a permanent colouring of the fibres by oxidation of oxidation dye precursors. The term oxidation dye precursor is a comprehensive term including what are known as developer components and coupler components. The developer components form the actual dyes with one another or with coupling to one or more coupler components, under the influence of oxidising agents or atmospheric oxygen. The oxidation dyes are characterised by excellent, long-lasting colouring results. For naturally acting dyes, a mixture from a larger number of oxidation dye precursors usually has to be used; in many cases, substantive dyes are also used to provide different shades of colour.

With regard to the dye precursors that can be used in the preparation (A) as contemplated herein, the present disclosure is not subject to any limitations. As dye precursors, the preparation (A) as contemplated herein can contain oxidation dye precursors of the developer and/or coupler type, and precursors of natural-like dyes, such as indole and indolin derivatives, and mixtures of representatives of these groups.

Within the scope of a first exemplary embodiment of the present disclosure, the preparation (A) as contemplated herein contains at least one oxidation dye precursor of the developer and/or coupler type.

The exemplary preparation (A) contains from about 0.5 to about 40 wt. %, such as from about 1.0 to about 35 wt. %, for example from about 5.0 to about 30 wt. %, such as from about 10 to about 25 wt. % of at least one oxidation dye precursor of the developer and/or coupler type, in each case in relation to the total amount of the preparation (A).

Certain embodiments as contemplated herein use a p-phenylenediamine derivative or a one of the physiologically acceptable salts thereof as developer component. Suitable p-phenylenediamines are selected from p-phenylenediamine, p-toluylenediamine, 2-chloro-p-phenylenediamine, N,N-bis-(2-hydroxyethyl)-p-phenylenediamine and N-phenyl-p-phenylenediamine, 2-(2-hydroxyethyl)-p-phenylenediamine, N-(4-amino-3-methylphenyl)-N-[3-(1H-imidazol-1-yl)propyl]amine and physiologically acceptable salts thereof. Suitable cosmetic products are exemplified in that preparation (A) contains at least one oxidation dye precursors of the developer type, such as at least one compound from the group of p-toluylenediamine, 2-(2-hydroxyethyl)-p-phenylenediamine, N,N-bis-(2-hydroxyethyl)-p-phenylenediamine, 2-methoxymethyl-p-phenylenediamine and/or physiologically acceptable salts thereof. In a further embodiment, compounds that contain at least two aromatic nuclei which are substituted with amino and/or hydroxyl groups are used as developer component. Suitable binuclear developer components are, in particular: N,N'-bis-(2-hydroxyethyl)-N,N'-bis-(4'-aminophenyl)-1,3-diamino-propan-2-ol and bis-(2-hydroxy-5-aminophenyl)-methane and physiologically acceptable salts thereof. Certain embodiments use p-toluylenediamine sulfate as developer component.

Furthermore, certain embodiments as contemplated herein use a p-aminophenol or a derivative thereof or of one of the physiologically acceptable salts thereof as developer component. Suitable p-aminophenols are in particular p-aminophenol, N-methyl-p-aminophenol, and 4-amino-3-methylphenol and physiologically acceptable salts thereof. The developer component can also be selected from o-aminophenol and derivatives thereof, such as 2-amino-5-methylphenol and physiologically acceptable salts thereof. Suitable cosmetic products are exemplified in that preparation (A) contains at least one oxidation dye precursor of the developer type, such as at least one compound from the group bis-(2-hydroxy-5-aminophenyl)methane, p-aminophenol, 4- and amino-3-methylphenol and/or physiologically acceptable salts thereof.

Lastly, the developer component can also be selected from heterocyclic developer components, such as the pyridine, pyrimidine, pyrazole, pyrazolo-pyrimidine derivatives and physiologically acceptable salts thereof. Suitable pyrimidine derivatives are in particular 2,4,5,6-tetraaminopyrimidine and 4-hydroxy-2,5,6-triaminopyrimidine and physiologically acceptable salts thereof. An exemplary pyrazole derivative is 4,5-diamino-1-(2-hydroxyethyl)pyrazole and physiologically acceptable salts thereof. Exemplary cosmetic products are exemplified in that preparation (A) contains at least one oxidation dye precursor of the developer type, such as at least one compound from the group 4,5-diamino-1-(2-hydroxyethyl)pyrazole, 2,4,5,6-tetraaminopyrimidine, 4-hydroxy-2,5,6-triaminopyrimidine and/or physiologically acceptable salts thereof.

In a further embodiment, the preparation (A) contains at least one coupler component.

Generally, m-phenylenediamine derivatives, naphthols, resorcinol and resorcinol derivatives, pyrazolones and m-aminophenol derivatives are used as coupler components. 1-naphthol, 1,5- and 2,7-dihydroxynaphthalene, 1-acetoxy-2-methoxynaphthalene, resorcinol, 4-chloro-resorcinol, 2-amino-3-hydroxypyridine and m-aminophenol and physiologically acceptable salts thereof are particularly suitable as coupler substances.

Exemplary coupler components as contemplated herein are
(A) m-aminophenol and/or derivatives thereof, such as 5-amino-2-methylphenol, 3-amino-2-chloro-6-methyl phenol, 5-amino-4-chloro-2-methylphenol, 5-(2'-hydroxyethyl)-amino-2-methylphenol and 2,4-dichloro-3-aminophenol,
(B) o-aminophenol and derivatives thereof, such as 2-amino-5-ethylphenol,
(C) m-diaminobenzene and derivatives thereof, such as 2,4-diaminophenoxyethanol, 1,3-bis-(2',4'-diaminophenoxy)propane, 1-methoxy-2-amino-4-(2'-hydroxyethylamino)benzene, 2,6-bis(2'-hydroxyethylamino)-1-methylbenzene, 2-({3-[(2-hydroxyethyl)amino]-4-methoxy-5-methylphenyl}amino)ethanol, and 2-({3-[(2-hydroxyethyl)amino]-2-methoxy-5-methylphenyl}-amino)ethanol,
(D) o-diaminobenzene and derivatives thereof,
(E) di- or trihydroxybenzene derivatives, such as 2-methylresorcinol, and 1,2,4-trihydroxybenzene,
(F) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxypyridine,
(G) naphthalene derivatives, such as 1-naphthol and 2-methyl-1-naphthol,
(H) morpholine derivatives, such as 6-hydroxybenzomorpholine,
(I) quinoxaline derivatives,
(J) pyrazole derivatives, such as 1-phenyl-3-methylpyrazol-5-one,
(K) indole derivatives, such as 6-hydroxyindol,
(L) pyrimidine derivatives, or
(M) methylenedioxybenzene derivatives, such as 1-(2'-hydroxyethyl)-amino-3,4-methylenedioxybenzene,
as well as the physiologically acceptable salts thereof.

Exemplary alternative cosmetic products are exemplified in that preparation (A) contains
at least one oxidation dye precursor of the coupler type, such as at least one compound from the group of 3-aminophenol, 5-amino-2-methylphenol, 3-amino-2-chloro-6-methylphenol, 2,4-dichloro-3-aminophenol and/or physiologically acceptable salts thereof;
at least one compound from the group of 2-(2,4-diaminophenoxy)ethanol, 1,3-bis(2,4-di-aminophenoxy)propane, 1-methoxy-2-amino-4-(2-hydroxyethylamino)

benzene, 2,6-bis(2'-hydroxyethylamino)-1-methylbenzene and/or physiologically acceptable salts thereof;

at least one compound from the group of resorcinol, 2-methylresorcinol and 4-chlororesorcinol;

at least one compound from the group of 2-amino-3-hydroxypyridine, 3-amino-2-methylamino-6-methoxypyridine, 2,6-dihydroxy-3,4-dimethylpyridine and/or physiologically acceptable salts thereof;

at least one compound from the group of 2-naphthol and 2,7-dihydroxynaphthalene.

Exemplary coupler components as contemplated herein are 3-aminophenol, 1-naphthol, 1,5- and 2,7-dihydroxynaphthalene, 5-amino-2-methylphenol, 2-amino-3-hydroxypyridine, resorcinol, 4-chlororesorcinol, 2-methylresorcinol and 2,6-dihydroxy-3,4-dimethylpyridine and physiologically acceptable salts thereof, wherein resorcinol and 3-aminophenol are particularly suitable in certain embodiments.

In an exemplary embodiment, the preparation (A) contains, as colorant, a combination of p-toluylenediamine or a physiologically acceptable salt thereof, in particular p-toluylenediamine sulfate, resorcinol and 3-aminophenol (m-aminophenol).

The exemplary preparation (A) contains p-toluylenediamine or a physiologically acceptable salt thereof, in particular p-toluylenediamine sulfate, in an amount of from about 0.5 to about 30 wt. %, resorcinol in an amount of from about 0.3 to about 18 wt. %, and m-aminophenol in an amount of from about 0.3 to about 6.0 wt. %, in each case in relation to the total amount of the preparation (A). An exemplary preparation (A) contains p-toluylenediamine or a physiologically acceptable salt thereof, in particular p-toluylenediamine sulfate, in an amount of from about 5 to about 15 wt. %, resorcinol in an amount of from about 3 to about 10 wt. %, and m-aminophenol in an amount of from 1.5 to 3.0 wt. %, in each case in relation to the total amount of preparation (A).

In a further embodiment of the present disclosure an exemplary preparation (A) contains, as oxidation dye precursor, at least one precursor of a natural-like dye. Indoles and indolines that comprise at least one hydroxy or amino group, such as a substituent on the six ring, may be used as precursors of natural-like dyes. Suitable derivatives of indoline are 5,6-dihydroxyindoline and 2,3-dioxoindoline (isatin) and physiologically acceptable salts thereof. An exemplary derivative of indole is 5,6-dihydroxyindole and physiologically acceptable salts thereof.

In addition to the oxidation dye precursors or alternatively to these colorants, the preparation (A) can also contain substantive dyes. In a further embodiment the preparation (A) contains at least one substantive dye. Substantive dyes can be divided into anionic, cationic and non-ionic substantive dyes. The substantive dyes may be selected from nitrophenylenediamines, nitroaminophenols, azo dyes, anthraquinones or indophenols and physiologically acceptable salts thereof.

2,4-dinitro-1-naphthol-7-sulfonic acid-disodium salt (C.l. 10,316; Acid Yellow 1; Food Yellow No. 1), 2-(indan-1,3-dion-2-yl)quinoline-x,x-sulfonic acid (mixture of mono- and disulfonic acid) (C.l. 47,005; D&C Yellow No. 10; Food Yellow No. 13; Acid Yellow 3, Yellow 10), 5-hydroxy-1-(4-sulfophenyl)-4-[(4-sulfophenyl)-azo]pyrazol-3-carboxylic acid-tri sodium salt (C.l. 19, 140; Food Yellow No. 4; Acid Yellow 23), 3-[(4-phenylamino)phenyl]azobezenesulfonic acid-sodium salt (C.l. 13,065; Ki406; Acid Yellow 36), 4-[(2-hydroxynaphth-1-yl)azo]-benzenesulfonic acid-sodium salt (C.l. 15,510; Acid Orange 7), 6-hydroxy-5-[(4-sulfonaphth-1-yl)azo]-2,4-naphthalenedisulfonic acid-trisodium salt (C.l. 16,255; Ponceau 4R; Acid Red 18), 8-amino-1-hydroxy-2-(phenylazo)-3,6-naphthalenedisulfonic acid-disodium salt (C.l. 17,200; Acid Red 33; Red 33), N-[6-(diethylamino)-9-(2,4-di sulfophenyl)-3H-xanthen-3-ylidene]-N-ethylethane ammonium hydroxide, inner salt, sodium salt (C.l. 45, 100; Acid Red 52), 2',4',5',7'-tetrabromo-4,5,6,7-tetrachloro-3',6'-dihydroxyspiro[isobenzofuran-1(3H),9'[9H]xanthen]-3-on-disodium salt (C.l. 45,410; Acid Red 92), 3-hydroxy-4-[(4-methyl-2-sulfonphenyl)azo]-2-naphthalenecarboxylic acid-calcium salt (C.l. 15,850:1; Pigment Red 57:1), 1,4-bis[(2-sulfo-4-methylphenyl)amino]-9, 10-anthraquinone-disodium salt (C.l. 61,570; Acid Green 25), bis[4-(dimethylamino)phenyl]-(3,7-disulfo-2-hydroxynaphth-1-yl)carbenium inner salt, sodium salt (C.l. 44,090; Food Green No. 4; Acid Green 50), N-[4-[(2,4-disulfophenyl)[4-[ethyl(phenylmethyl)amino) phenyl]methylene]-2,5-cyclohexadien-1-yliden]-N-ethyl benzenemethanaminium hydroxide, inner salt, sodium salt (C.l. 42,080; Acid Blue 7), (2-sulfophenyl)di[4-(ethyl((4-sulfophenyl)methyl)amino)phenyl]-carbenium-disodium salt betaine (C.l. 42,090; Acid Blue 9; FD&C Blue No. 1), 1-amino-4-(cyclohexylamino)-9,10-anthraquinone-2-sulfonic acid-sodium salt (C.l. 62045; Acid Blue 62), 1-hydroxy-4-[(4-methyl-2-sulfophenyl)amino]-9,10-anthraquinone-sodium salt (C.l. 60,730; D&C Violett No. 2; Acid Violet 43), 5-amino-4-hydroxy-6-[(4-nitrophenyl)-azo]-3-(phenylazo)-2,7-naphthalenedisulfonic acid-disodium salt (C.l. 20,470; Acid Black 1), 3-hydroxy-4-[(2-hydroxynaphth-1-yl)azo]-7-nitro-1-naphthalenesulfonic acid-chromium complex (3:2) (C.l. 15,711; Acid Black 52), and 3',3",4,5,5',5",6,7-octabromophenolsulfonphthalein (tetrabromphenol blue) are particularly suitable as anionic substantive dyes.

Suitable anionic substantive dyes are the compounds known by the international names or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Di[4-(diethylamino)phenyl][4-(ethylamino)naphthyl]carbenium chloride (C.l. 42,595; Basic Blue 7), di[4-(dimethylamino)phenyl][4-(phenylamino)naphthyl] carbenium chloride (C.l. 44,045; Basic Blue 26), 8-amino-2-bromo-5-hydroxy-4-imino-6-[(3-(trimethylammonio)phenyl) amino]-1 (4H)-naphthalinone chloride (C.l. 56,059; Basic Blue No. 99), tri(4-amino-3-methylphenyl)carbenium chloride (C.l. 42,520; Basic Violet 2), di(4-aminophenyl)(4-amino-3-methylphenyl)carbenium chloride (C.l. 42,510 Basic Violet 14), 1-[(4-aminophenyl)azo]-7-(trimethylammonio)-2-naphthol chloride (C.l. 12,250; Basic Brown 16), 1-[(4-amino-3-nitrophenyl)azo]-7-(trimethylammonio)-2-naphthol chloride (C.l. 12,251; Basic Brown 17), 3-[(4-amino-2,5-dimethoxyphenyl)azo]-N,N,N-trimethylbenzenaminium chloride (C.l. 12,605, Basic Orange 69), 2-[((4-dimethylamino)phenyl)azo]-1,3-dimethyl-1H-imidazolium chloride (Basic Red 51), 2-hydroxy-1-[(2-methoxyphenyl) azo]-7-(trimethylammonio)-naphthalene chloride (C.l. 12,245; Basic Red 76), 2-[4-aminophenyl]azo]-1,3-dimethyl-1H-imidazolium chloride (Basic Orange 31), 3-methyl-1-phenyl-4-[(3-(trimethylammonio)phenyl)azo]-pyrazol-5-one chloride (C.l. 12,719; Basic Yellow 57), 1-methyl-4-((methylphenylhydrazono)methyl)-pyridinium methylsulfate (Basic Yellow 87), 1-(2-morpholiniumpropylamino)-4-hydroxy-9, 10-anthraquinone-methylsulfate, 4-formyl-1-methylquinolonium-p-toluenesulfonate and substantive dyes that contain a heterocycle comprising at least one quaternary nitrogen atom are particularly suitable as cationic substantive dyes.

Non-ionic nitro and quinone dyes and neutral azo dyes are particularly suitable as non-ionic substantive dyes.

Suitable blue nitro dyes are, in particular, 1,4-bis[(2-hydroxyethyl)amino]-2-nitrobenzene (HC Violet B S), 1-(2-hydroxyethyl)amino-2-nitro-4-[di(2-hydroxyethyl)amino]-benzene (HC Blue 2), 4-[di(2-hydroxyethyl)amino]-1-[(2-methoxyethyl)amino]-2-nitrobenzene (HC Blue 11), 4-[ethyl-(2-hydroxyethyl)-amino]-1-[(2-hydroxyethyl)amino]-2-nitrobenzene-hydrochloride (HC Blue 12), 1-(2-hydroxyethyl)amino-2-nitro-4-N-ethyl-N-(2-hydroxyethyl)aminobenzene (HC Blue 15), 1-amino-3-methyl-4-[(2-hydroxyethyl)amino]-6-nitrobenzene (HC Violet 1), and 1-(3-hydroxypropylamino)-4-[di(2-hydroxyethyl)amino]-2-nitrobenzene (HC Violet 2).

Suitable red nitro dyes are, in particular, 1-amino-4-[(2-hydroxyethyl)amino]-2-nitrobenzene (HC Red 7), 2-amino-4,6-dinitrophenol (picramic acid) and salts thereof, 1,4-diamino-2-nitrobenzene (C.l. 76,070), 4-amino-2-nitrodiphenylamine (HC Red 1), 1-amino-4-[di(2-hydroxyethyl)amino]-2-nitrobenzene hydrochloride (HC Red 13), 1-amino-4-[(2-hydroxyethyl)-amino]-5-chloro-2-nitrobenzene, 4-amino-1-[(2-hydroxyethyl)amino]-2-nitrobenzene (HC Red 3), 4-[(2-hydroxyethyl)-amino]-3-nitrotoluene, 4-amino-3-nitrophenol, 4-[(2-hydroxyethyl)-amino]-3-nitrophenol, 4-[(2-nitrophenyl)amino]phenol (HC Orange 1), 1-[(2-aminoethyl)amino]-4-(2-hydroxyethoxy)-2-nitrobenzene (HC Orange 2), 1-amino-5-chloro-4-[(2,3-dihydroxypropyl)amino]-2-nitrobenzene (HC Red 10), 5-chloro-1,4-[di(2,3-dihydroxypropyl)amino]-2-nitrobenzene (HC Red 11), 2-[(2-hydroxyethyl)amino]-4,6-dinitrophenol and salts thereof, 4-ethylamino-3-nitrobenzoic acid, 2-[(4-amino-2-nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol (HC Red BN), 1,2,3,4-tetrahydro-6-nitroquinoxaline, and 6-hydroxy-5-((2-methoxy-5-methyl-4-sulfophenyl)azo)-2-naphthalenesulfonic acid (Curry Red).

Suitable yellow nitro dyes are, in particular, 1,2-diamino-4-nitrobenzene (C.l. 76,020), 1-[(2-hydroxyethyl)amino]-2-nitrobenzene (HC Yellow 2), 1-(2-hydroxyethoxy)-2-[(2-hydroxyethyl)amino]-5-nitrobenzene (HC Yellow 4), 1-amino-2-[(2-hydroxyethyl)amino]-5-nitrobenzene (HC Yellow 5), 4-[(2,3-dihydroxypropyl)-amino]-3-nitro-1-trifluoromethyl-benzene (HC Yellow 6), 2-[(2-hydroxyethyl)amino]-1-methoxy-5-nitrobenzene, 2-amino-4-nitrophenol, 1-(2-hydroxyethoxy)-3-methylamino-4-nitrobenzene, 2,3-(dihydroxypropoxy)-3-methylamino-4-nitrobenzene, 3-[(2-aminoethyl)amino]-1-methoxy-4-nitrobenzene-hydrochloride (HC Yellow 9), 1-chloro-2,4-bis[(2-hydroxyethyl)amino]-5-nitrobenzene (HC Yellow 10), 2-[(2-hydroxyethyl)amino]-5-nitrophenol (HC Yellow 11), 1-[(2'-ureidoethyl)amino]-4-nitrobenzene, 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow 12), and 4-[(2-hydroxyethyl)amino]-3-nitro-1-trifluormethyl benzene (HC Yellow 13).

Suitable quinone dyes are, in particular, 1-[(2-hydroxyethyl)amino]-4-methylamino-9,10-anthraquinone (C.l. 61,505, Disperse Blue 3), mixtures of 1,4-bis[(2-hydroxyethyl)amino]anthra-9,10-quinone with 1-[(2-hydroxyethyl)amino]-4-[(3-hydroxypropyl)amino]anthra-9,10-quinone and 1,4-bis[(3-hydroxypropyl)amino]anthra-9,10-quinone (Disperse Blue 377), 1,4-diamino-9,10-anthraquinone (C.l. 61,100, Disperse Violet 1), 1-amino-4-(methylamino)-9,10-anthraquinone (C.l. 61,105, Disperse Violet 4, Solvent Violet No. 12), 2-hydroxy-1,4-naphthoquinone (Lawsone, C.l. 75,480, Natural Orange 6), and 1,4-bis[(2,3-dihydroxypropyl)amino]-9,10-anthracenedione (HC Blue 14).

Suitable neutral azo dyes are, in particular, 1-[di(2-hydroxyethyl)amino]-3-methyl-4-[(4-nitrophenyl)azo]-benzene (C.l. 11,210, Disperse Red 17), 1-[di(2-hydroxyethyl)amino]-4-[(4-nitrophenyl)azo]-benzene (Disperse Black 9), 4-[(4-aminophenyl)azo]-1-[di(2-hydroxyethyl)amino]-3-methylbenzene (HC Yellow 7), 2,6-diamino-3-[(pyridin-3-yl)azo]-pyridine, 4-[(4-nitrophenyl)azo]-aniline (C.l. 11,005; Disperse Orange 3).

As oxidising agent, the preparation (B) contains percarbamide (addition compound of hydrogen peroxide and urea), percarbonate (2 $Na_2CO_3$ 0.3 $H_2O_2$) and/or perborate (sodium perborate) in a total amount of from about 0.5 to about 95 wt. %, such as from about 20 to about 60 wt. %, for example from about 35 to about 55 wt. %, such as from about 40 to about 50 wt. %, in relation to its total weight. In certain embodiments, only percarbamide is used as the oxidising agent of preparation (B).

As further constituent, the exemplary preparation (A) and/or exemplary preparation (B) contains a filler. In an exemplary embodiment, the filler is powdered. As contemplated herein, magnesium carbonate is an exemplary filler. In certain embodiments, the preparation (B) does not contain any further constituents apart from the oxidising agent and the filler. The amount of filler in exemplary preparation (A) ranges from about 5 to about 30 wt. %, such as from about 10 to about 20 wt. %, in relation to the total weight of the preparation (A). The amount of filler in exemplary preparation (B) ranges from about 25 to about 99.5 wt. %, such as from about 40 to about 80 wt. %, for example from about 45 to about 65 wt. %, such as from about 50 to about 60 wt. %, in relation to the total weight of preparation (B).

So as to be able to apply the mixture for use formed of preparations (A) and (B) cleanly and in a locally restricted manner, a higher viscosity of the product is advantageous. To this end, it is advantageous if the product is not provided in the form of a paste, viscous cream or thickened gel, but instead has a sufficient flowability. Furthermore, the ready-to-use product must have rheological properties that allow an application to the fibres to be bleached, but at the same time prevent a running or flowing away of the product from the site of action during the period of application. The exemplary mixtures for use therefore have a viscosity of from about 5 to about 100 Pa·s, such as from about 10 to about 50 Pa·s, for example from about 10 to about 20 Pa·s, such as from about 10 to about 16 Pa·s (Brookfield, 22° C., spindle #5, 4 rpm). To this end, exemplary preparations (A) or (B), such as only (A), contain at least one thickening agent and/or at least one gelling agent. Inorganic and organic substances are suitable as thickening agents and gelling agents. In certain embodiments, the thickening agents and gelling agents are part of preparation (B).

The thickening agents can be selected by way of example from the polymeric thickening agents known under the following INCI names: Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C 10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, *Astragalus* Gummifer Gum, Attapulgite, *Avena Sativa* (Oat) Kernel Flour, Bentonite, Butoxy Chitosan, *Caesalpinia Spinosa* Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl hydroxyethylcellulose, Carboxymethyl hydroxypropyl Guar, Cellulose Acetate Propionate Carboxylate, Cellulose Gum, *Ceratonia Siliqua* Gum, Cetyl hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/lsophthalates/SIP Copolymer, dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar hydroxypropyltrimonium Chloride, Hectorite, Hydrated Silica, Hydrogenated Potato Starch, hydroxybutyl Methylcellulose, hydroxyethyl Acrylate/Sodium Acryloyldimethyl Taurate Copolymer, hydroxyethylcellulose, hydroxyethyl Chitosan, hydroxyethyl Ethylcellulose, hydroxypropylcellulose, hydroxypropyl Chitosan, hydroxypropyl Ethylenediamine Carbomer, hydroxypropyl Guar, hydroxypropyl Methylcellulose, hydroxypropyl Methylcellulose Stearoxy Ether, hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl hydroxyethylcellulose, Microcrystalline Cellulose, Montmorillonite, Moroccan Lava Clay, Natto Gum, Nonoxynyl hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-1 15M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MACopolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, *Sclerotium* Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, and *Zea Mays* (Corn) Starch.

In exemplary embodiments, the thickening agent or the gelling agent is selected from polyacrylic acid, carboxymethylcellulose, silica, a copolymer of methacrylic acid and methyl methacrylate, and a combination thereof.

In exemplary embodiments, the combination of polyacrylic acid and silica is a constituent of the preparation (B).

In exemplary embodiments, the polymeric thickening agents and gelling agents are contained in the preparation (B) in a total amount of from about 0.1 to about 10 wt. %, in particular from about 0.4 to about 5.0 wt. %.

The selection of the amount and chemical nature of the thickening agents and gelling agents not only influences the viscosity of the mixture for use formed of preparation (A) and (B), but additionally also the dissolution properties of the preparations (A) and (B). The aforementioned suitable thickening agents/gelling agents also may have a particularly advantageous effect on the dissolution properties of the preparations (A) and (B).

The composition of some cosmetic products as contemplated herein can be found in the following tables (values in wt. % relate to the total weight of the preparations (A) and (B) unless specified otherwise).

|  | Formula 1 | Formula 2 | Formula 3 | Formula 4 |
| --- | --- | --- | --- | --- |
|  | preparation (A) | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |

-continued

|  | preparation (B) | | | |
|---|---|---|---|---|
| percarbamide, percarbonate and/or perborate | 0.5 to 95 | 20 to 60 | 35 to 55 | 40 to 50 |
| further ingredients | to 100 | to 100 | to 100 | to 100 |

|  | Formula 6 | Formula 7 | Formula 8 | Formula 9 |
|---|---|---|---|---|
|  | preparation (A) | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide, percarbonate and/or perborate | 0.5 to 95 | 20 to 60 | 35 to 55 | 40 to 50 |
| further ingredients | to 100 | to 100 | to 100 | to 100 |

|  | Formula 11 | Formula 12 | Formula 13 | Formula 14 |
|---|---|---|---|---|
|  | preparation (A) | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide | 0.5 to 95 | 20 to 60 | 35 to 55 | 40 to 50 |
| further ingredients | to 100 | to 100 | to 100 | to 100 |

|  | Formula 16 | Formula 17 | Formula 18 | Formula 19 |
|---|---|---|---|---|
|  | preparation (A) | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide | 0.5 to 95 | 20 to 60 | 35 to 55 | 40 to 50 |
| further ingredients | to 100 | to 100 | to 100 | to 100 |

|  | Formula 21 | Formula 22 | Formula 23 | Formula 24 |
|---|---|---|---|---|
|  | preparation (A) | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide, percarbonate and/or perborate | 0.5 to 95 | 20 to 60 | 35 to 55 | 40 to 50 |
| thickener and/or gelling agent | 0.1 to 10 | 0.2 to 8.0 | 0.3 to 6.0 | 0.4 to 5.0 |
| further ingredients | to 100 | to 100 | to 100 | to 100 |

|  | Formula 26 | Formula 27 | Formula 28 | Formula 29 |
|---|---|---|---|---|
|  | preparation (A) | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide, percarbonate and/or perborate | 0.5 to 95 | 20 to 60 | 35 to 55 | 40 to 50 |
| thickener and/or gelling agent | 0.1 to 10 | 0.2 to 8.0 | 0.3 to 6.0 | 0.4 to 5.0 |
| further ingredients | to 100 | to 100 | to 100 | to 100 |

|  | Formula 31 | Formula 32 | Formula 33 | Formula 34 |
|---|---|---|---|---|
|  | preparation (A) | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide | 0.5 to 95 | 20 to 60 | 35 to 55 | 40 to 50 |
| thickener and/or gelling agent | 0.1 to 10 | 0.2 to 8.0 | 0.3 to 6.0 | 0.4 to 5.0 |
| further ingredients | to 100 | to 100 | to 100 | to 100 |

|  | Formula 36 | Formula 37 | Formula 38 | Formula 39 |
|---|---|---|---|---|
|  | preparation (A) | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide | 0.5 to 95 | 20 to 60 | 35 to 55 | 40 to 50 |
| thickener and/or gelling agent | 0.1 to 10 | 0.2 to 8.0 | 0.3 to 6.0 | 0.4 to 5.0 |
| further ingredients | to 100 | to 100 | to 100 | to 100 |

|  | Formula 41 | Formula 42 | Formula 43 | Formula 44 |
|---|---|---|---|---|
|  | preparation (A) | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
|  | preparation (B) | | | |
| percarbamide, percarbonate and/or perborate | 0.5 to 95 | 20 to 60 | 35 to 55 | 40 to 50 |
| polyacrylic acid and/or silica | 0.1 to 10 | 0.2 to 8.0 | 0.3 to 6.0 | 0.4 to 5.0 |
| further ingredients | to 100 | to 100 | to 100 | to 100 |

-continued

|  | Formula 46 | Formula 47 | Formula 48 | Formula 49 |
|---|---|---|---|---|
| preparation (A) | | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
| preparation (B) | | | | |
| percarbamide, percarbonate and/or perborate | 0.5 to 95 | 20 to 60 | 35 to 55 | 40 to 50 |
| polyacrylic acid and/or silica | 0.1 to 10 | 0.2 to 8.0 | 0.3 to 6.0 | 0.4 to 5.0 |
| further ingredients | to 100 | to 100 | to 100 | to 100 |

|  | Formula 51 | Formula 52 | Formula 53 | Formula 54 |
|---|---|---|---|---|
| preparation (A) | | | | |
| colorant | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
| preparation (B) | | | | |
| percarbamide | 0.5 to 95 | 20 to 60 | 35 to 55 | 40 to 50 |
| polyacrylic acid and/or silica | 0.1 to 10 | 0.2 to 8.0 | 0.3 to 6.0 | 0.4 to 5.0 |
| further ingredients | to 100 | to 100 | to 100 | to 100 |

|  | Formula 56 | Formula 57 | Formula 58 | Formula 59 |
|---|---|---|---|---|
| preparation (A) | | | | |
| oxidation dye precursor | 0.5 to 40 | 1.0 to 35 | 5.0 to 30 | 10 to 25 |
| hydrated sodium silicate | 20 to 80 | 25 to 78 | 30 to 76 | 35 to 75 |
| further ingredients | to 100 | to 100 | to 100 | to 100 |
| preparation (B) | | | | |
| percarbamide | 0.5 to 95 | 20 to 60 | 35 to 55 | 40 to 50 |
| polyacrylic acid and/or silica | 0.1 to 10 | 0.2 to 8.0 | 0.3 to 6.0 | 0.4 to 5.0 |
| further ingredients | to 100 | to 100 | to 100 | to 100 |

The preparations (A) and (B) are provided packaged separately in a water-soluble film, such as in a two-chamber bag (pouch), in which both preparations are packaged separately from one another, but with the chambers being connected to one another by film or the chambers having a film disposed therebetween as a partitioning wall. The present disclosure, however, also comprises embodiments, or what are known as kits-of-parts, in which the preparations (A) and (B) are packaged separately from one another, in each case in a water-soluble film and the chambers are not connected to one another. In particular in the last-mentioned cases, the preparations (A) and (B) are packaged in the same or different water-soluble films.

Water-soluble films are known per se. In respect of the dissolution rate and also the consistency of the resultant mixture for use, an exemplary water-soluble film contains a polymer mixture of which the molecular weight distribution is multimodal. In other words, the density of the frequency distribution of the molecular weight has at least two modes (maxima), for example two, three, four, five or more modes.

A bimodal molecular weight distribution may have, as described in the introduction, a very advantageous effect on the product properties of cosmetic products as contemplated herein and also can be provided more easily than a tri- or multimodal frequency distribution.

An exemplary bimodal molecular weight distribution can be symmetrical or asymmetrical.

In an exemplary multimodal, such as bimodal, molecular weight distribution, the molecular weights of at least two of the modes differ from one another, based on the smallest molecular weight that can be assigned to a mode, by from about 5% to about 120%, such as by from about 10% to about 90%, and in particular by from about 20% to about 60%.

In a further exemplary multimodal, such as bimodal, molecular weight distribution, the frequency of the minimums between two modes differs from the frequency of the smallest of these two modes (mode with the lowest frequency) by from about 5% to about 80%, such as from about 10% to about 60%, and in particular from about 20% to about 40%, in each case based on the frequency of the smallest of the two modes. For the application properties of products as contemplated herein, in particular the rapid and residue-free production of the hair-cosmetic mixture for use, it has proven to be advantageous if the water-soluble film, in relation to its total weight, consists to an extent of at least 70 wt. %, such as to an extent of at least 80 wt. %, for example to an extent of at least 90 wt. %, such as to an extent of at least 95 wt. % of a polymer mixture having a multimodal molecular weight distribution. Again, a bimodal molecular weight distribution is provided in an exemplary embodiment.

Polymer mixtures which have a polydispersity index above 2.2, such as above 3.0, for example above 4.6 have proven to be advantageous for the product properties. Here, the ratio of weight average and number average molar mass is referred to as the polydispersity index.

The weight average or the weight average molar mass ($M_{av}$) is defined as $$M_{av} = \Sigma n_i M_i^2 / n_i M_i$$

with $M_{av}$=weight average molar mass, ni=number of the macromolecules in the sample with exactly i repetition units and Mi=molar mass i.

The weight average is obtained by methods which take into consideration the size and form of a molecule in solution, for example static light scattering, X-ray small-angle scattering and sedimentation balance measurements.

The number average or the number average molar mass ($M_n$) is defined as $$M_n = \Sigma n_i M_i^2 / n_i M_i$$

with $M_n$=number average molar mass, ni=number of the macromolecules in the sample with exactly i repetition units, and Mi=molar mass i.

The number average can be determined by colligative methods, such as cryoscopy, membrane or vapour pressure osmometry, and—provided the number of end groups per molecule is known—by end-group determination.

Water-soluble films which do not consist entirely of the polymer mixture with the multimodal molecular weight distribution can contain additional active agents or fillers, but also solvents, in particular water, as further ingredients.

Here, constituents that are effective in the field of hair cosmetics for example as well as materials which protect the ingredients of preparation (A) enclosed by the film material against breakdown or deactivation caused by exposure to light are also included in the group of further active agents. Here, antioxidants, UV absorbers and fluorescence dyes have proven to be particularly suitable. An exemplary water-soluble film has a water content, in relation to its total weight, of from about 3.0 to about 12 wt. %, such as from about 4.0 to about 10 wt. %.

The thickness of exemplary water-soluble film(s) used for the packaging of the preparations (A) and (B) is from about 0.01 to about 0.1 mm, such as from about 0.01 to about 0.08 mm, for example from about 0.02 to about 0.06 mm.

The water-soluble film in which the preparations (A) and (B) are packaged can comprise one or more structurally different water-soluble polymers. In particular, polymers from the group of (possibly acetalised) polyvinyl alcohols (PVALs), polyvinylpyrrolidones, polyethylene oxides, gelatines and celluloses are suitable as water-soluble polymer(s).

In a first exemplary embodiment, the polymer mixture with the multimodal, such as bimodal, molecular weight distribution comprises two vinyl acetate/vinyl alcohol copolymers. Exemplary cosmetic products are therefore exemplified in that the polymer mixture, in relation to its total weight, consists to an extent of at least 60 wt. %, such as to an extent of at least 80 wt. %, for example to an extent of at least 90 wt. %, such as to an extent of at least 95 wt. % of a mixture comprising a1) water-soluble vinyl alcohol/vinyl acetate copolymer a1) and a2) at least one water-soluble vinyl alcohol/vinyl acetate copolymer a2) different from the water-soluble vinyl alcohol/vinyl acetate copolymer a1).

In the aforementioned exemplary embodiment based on two water-soluble vinyl alcohol/vinyl acetate copolymers, the exemplary polymer mixture has a polydispersity index above 2.2, such as above 3.0, and in particular above 4.6, whereas the polydispersity index of the exemplary vinyl alcohol/vinyl acetate copolymer a1) lies between about 1.8 and about 2.3.

Particularly advantageous product properties may be attained by vinyl alcohol/vinyl acetate copolymers a1) with a degree of hydrolysis between about 84% and about 90%, such as between about 85% and about 89%, for example between about 86% and about 88%. Corresponding copolymers a1) in other words have a residual content of acetyl groups between about 10% and about 16%, such as between about 11% and about 15%, for example between about 12% and about 14%.

Besides the polydispersity index and the degree of hydrolysis, the viscosity of aqueous solutions of the vinyl alcohol/vinyl acetate copolymers has proven to be a exemplary feature of particularly advantageous copolymers. Exemplary cosmetic products are therefore exemplified in that the vinyl alcohol/vinyl acetate copolymer a1) has a viscosity (20° C., 4 wt. % solution in water, measured using a Brookfield LV Viscosimeter with UL adapter) between 12 cP and 20 cP, such as between 14 cP and 19 cP, for example between 16 cP and 18 cP.

By contrast, the viscosity (20° C., 4 wt. % solution in water, measured using a Brookfield LV Viscosimeter with UL adapter) of the exemplary vinyl alcohol/vinyl acetate copolymer a2) is between about 20 cP and about 30 cP, such as between about 20 cP and about 28 cP, for example between about 20 cP and about 25 cP.

Besides the combinations described above of two vinyl alcohol/vinyl acetate copolymers, there are further exemplary polymer combinations that have advantageous properties in view of the above-mentioned technical objectives. In an alternative embodiment of cosmetic products as contemplated herein, the polymer mixture of the water-soluble film, in relation to its total weight, consists to an extent of at least 60 wt. %, such as to an extent of at least 80 wt. %, for example to an extent of at least 90 wt. %, such as to an extent of at least 95 wt. % of a mixture comprising a1) water-soluble vinyl alcohol/vinyl acetate copolymer a1) and a2) at least one, possibly modified, water-soluble polysaccharide, such as at least one water-soluble polysaccharide from the group of methylcellulose, carboxymethylcellulose, ethyl cellulose, hydroxyethyl cellulose, hydroxypropyl cellulose, hydroxypropyl methylcellulose, dextrin and hydroxypropyl starch, for example at least one water-soluble polysaccharide from the group of hydroxypropyl starches.

The polydispersity index of the aforementioned exemplary polymer mixtures of vinyl alcohol/vinyl acetate copolymers and polysaccharide again lies above 2.2, such as above 3.0, for example above 4.6, whereas the vinyl alcohol/vinyl acetate copolymer a1) in these exemplary mixtures has a polydispersity index between about 1.8 and about 2.3.

If the vinyl alcohol/vinyl acetate copolymer a1) is combined with a polysaccharide, the vinyl alcohol/vinyl acetate copolymer a1) may have a degree of hydrolysis between about 84% and about 90%, such as between about 85% and about 89%, for example between about 86% and about 88%. The viscosity (20° C., 4 wt. % solution in water, measured using a Brookfield LV Viscosimeter with UL adapter) of the exemplary vinyl alcohol/vinyl acetate copolymer a1) lies between about 12 cP and about 20 cP, such as between about 14 cP and about 19 cP, for example between about 16 cP and about 18 cP.

As mentioned above, the viscosity of the mixture for use lies in selected viscosity ranges. The viscosity of the mixture for use obtainable by mixing the preparations (A) and (B) can be adjusted by the selection of a suitable polymer mixture for the water-soluble film. The viscosity of the mixture for use and application properties thereof and bleaching effect can be advantageously influenced here both by the chemical nature of the polymer mixture and by the amount of the polymer mixture used for the packaging. Exemplary cosmetic products are therefore exemplified in that the proportion by weight of the polymer mixture having the multimodal molecular weight distribution in the total weight of the preparations (A) and (B) inclusive of the water-soluble film is from about 1 to about 15 wt. %, such as from about 2 to about 10 wt. %, for example from about 3 to about 8 wt. %.

In exemplary embodiments, the preparation (A) and/or preparation (B), such as only preparation (A), can also contain further active agents, auxiliaries and additives, such as non-ionic polymers, for example vinylpyrrolidone/vinyl acrylate copolymers, polyvinylpyrrolidone and vinylpyrrolidone/vinyl acetate copolymers and polysiloxanes, cationic polymers, such as quaternised cellulose ethers, polysiloxanes with quaternary groups, dimethyldiallyl ammonium chloride polymers, acrylamide-dimethyldiallyl ammonium chloride copolymers, dimethylaminoethyl methacrylate-vinylpyrrolidone copolymers quaternised with diethyl sulfate, vinylpyrrolidone-imidazolinium methochloride copolymers and quaternised polyvinyl alcohol, zwitterionic and amphoteric polymers, such as acrylamidopropyl-trimethylammonium chloride/acrylate copolymers and octylacrylamide/methyl-methacrylate/tert-butylaminoethylmethacrylate/2-hydroxypropylmethacrylate copolymers, anionic polymers, such as polyacrylic acids, cross-linked polyacrylic acids, vinyl acetate/crotonic acid copolymers, vinylpyrrolidone/ vinyl acrylate copolymers, vinyl acetate/butyl maleate/ isobornyl acrylate copolymers, methylvinylether/maleic acid anhydride copolymers and acrylic acid/ethylacrylate/ N-tert.butyl-acrylamide terpolymers, solvents and solubilising agents, such as ethanol, isopropanol, ethylene glycol, propylene glycol, glycerol and diethylene glycol, consistency enhancers, such as sugar esters, polyol esters or polyolalkyl ethers, stabilisers, for example complexing agents, such as EDTA, NTA, β-alanine diacetic acid and phosphonic acids, and/or pH-regulators, such as ammonium chlorides.

In an exemplary embodiment, the preparations (A) and (B) are provided in solid form, for example in the form of a powder, a granulate, or a compacted body, for example in the form of a tablet. The preparations (A) and (B) are provided in powder form in certain embodiments.

In exemplary embodiments, the preparations (A) and (B) are anhydrous as contemplated herein. The term "anhydrous" means a water content of 1 wt. % or less as contemplated herein. In an exemplary embodiment, the preparations (A) and (B) have a water content of 0.5 wt. % or less, such as 0.2 wt. % or less, for example 0.1 wt. % or less, such as close to 0 or 0 wt. %, wherein in each case the content of free, i.e. unbound water is meant. The content of free water can be determined by employing the Karl-Fischer method as contemplated herein.

In an exemplary embodiment, the ratio by weight of preparation (A) to preparation (B) in the separate packagings ranges from about 10:1 to about 1:10, such as from about 5:1 to about 1:5, for example from about 3:1 to about 1:3, such as approximately 3:2.

The present disclosure also relates to a method for dyeing keratin fibres using the cosmetic product. In the method as contemplated herein, a mixture for use is prepared at least from the two preparations (A) and (B) packaged separately from one another by placing the preparations (A) and (B) packaged in a water-soluble film in water in order to dissolve the water-soluble films, and by then treating keratin fibres with the mixture for use in the usual way.

In an exemplary embodiment, the volume ratio of the totality of preparations (A) and (B) to the water is from about 1:1 to about 1:6, such as from about 1:2 to about 1:3, for example approximately 1:2.

In exemplary embodiments, the preparations (A) and (B) are packaged connected to one another in a two-chamber bag (pouch) so that the two-chamber bag is placed in water in order to produce the mixture for use easily.

As contemplated herein, the mixture for use can be applied to the keratin-containing fibres, left on the fibres at a temperature of from room temperature to 45° C. for a reaction time of from about 10 to about 60 minutes, and then rinsed out again with water or washed out with a shampoo.

The reaction time of the ready-to-use lightener is from about 10 to about 16 min, in particular from about 15 to about 50 min, such as from about 20 to about 45 min, in exemplary embodiments. During the reaction time of the product on the fibres, it can be advantageous to assist the colouring process by adding heat.

The heat can be added by an external heat source, for example with the aid of a hot air fan, and also, in particular when lightening the hair of living subjects, by the body temperature of the subject. In the case of the latter possibility, the area to be lightened is usually covered by a hood. A reaction phase at room temperature also corresponds to embodiments herein. In an exemplary embodiment, the temperature during the reaction time is between about 20° C. and about 40° C., in particular between about 25° C. and about 38° C. The lighteners provide good colouring results already at physiologically acceptable temperatures of below 45° C.

At the end of the reaction time, the remaining colouring preparation is rinsed from the hair using water or a cleansing product. Here, commercially available shampoo in particular can be used as a cleansing product, wherein in particular the cleansing product can then be omitted and the rinsing process can be performed using mains water if the mixture for use contains sufficient surfactants.

The dissolving of the films and the mixing of both preparations is generally assisted by stirring. Following careful stirring or mixing, the mixture for use is generally applied to the hair with the aid of a brush or an applicator.

Examples

The preparations (A) and (B) presented in the following Tables 1 and 2 were prepared. The values for the amounts are in wt. %.

TABLE 1

| Constituent | Preparation (A) |
| --- | --- |
| p-toluylenediamine sulfate | 12.2 |
| resorcinol | 4.5 |
| m-aminophenol | 1.5 |
| ammonium chloride | 6.0 |
| Britesil C265 | 60.6 |
| Luvomag ® C 013 | 15.2 |
| total | 100 |

Ingredients:
Luvomag® C 013 (Lehmann&Voss&Co.): magnesium carbonate

TABLE 2

| Constituent | Preparation (B) |
| --- | --- |
| percarbamide | 34.0 |
| magnesium carbonate | 64.8 |
| polyacrylic acid | 0.8 |
| hydrophilic silica, BET | 0.4 |
| Total | 100 |

The preparations (A) and (B) were packaged in a two-chamber container formed from a water-soluble film, wherein the ratio by weight of preparation (A) to preparation (B) was 1:1.

The two-chamber bag was placed in water, which was provided in a volume ratio of approximately 1 (bag) to 2 (water). With stirring, a mixture for use was obtained within a few minutes.

The mixture for use was applied to human hair and demonstrated good properties, such as ease of spreading, consistency after the mixing, feel on the scalp, and in particular a very good colour result.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for dyeing keratin fibers comprising:
   a preparation (A) and a preparation (B), wherein preparations (A) and (B) are packaged separately from one another and wherein the preparations (A) and (B) are packaged in a water-soluble film, wherein the preparation (A) comprises:
   (a) at least one colorant from the group of oxidation dye precursors and substantive dyes; and
   (b) hydrated sodium silicate in an amount of from about 20 to about 80 wt. %, in relation to the total weight of preparation (A); and
   wherein the preparation (B), in relation to its total weight, comprises at least one member from the group of percarbamide, percarbonates and perborates, in a total amount of from about 0.5 to about 95 wt. %.

2. The cosmetic product according to claim 1, wherein the cosmetic product is produced as a two-chamber bag having a first chamber and a second chamber, and wherein the preparation (A) is in the first chamber and the preparation (B) is in the second chamber.

3. The cosmetic product according to claim 1, wherein the hydrated sodium silicate has a molar ratio $Na_2O:SiO_2$ of from about 1:2 to about 1:3.

4. The cosmetic product according to claim 1, wherein the preparation (A), as colorant, comprises:
   p-toluylenediamine or a physiologically acceptable salt thereof in an amount of from about 0.5 to about 30 wt. %, in relation to the total amount of the preparation (A);
   resorcinol in an amount of from about 0.3 to about 18 wt. %, in relation to the total amount of the preparation (A); and
   m-aminophenol in an amount of from about 0.3 to about 6.0 wt. %, in relation to the total amount of the preparation (A).

5. The cosmetic product according to claim 4, wherein the preparation (A), as colorant, comprises resorcinol in an amount of from about 3 to about 10 wt. %.

6. The cosmetic product according to claim 4, wherein the preparation (A), as colorant, comprises m-aminophenol in an amount of from about 1.5 to about 3.0 wt. %.

7. The cosmetic product according to claim 1, wherein the preparation (A) comprises:
   p-toluylenediamine disulfate in an amount of from about 5 to about 15 wt. %, in relation to the total weight of the preparation (A);
   resorcinol in an amount of from about 3 to about 10 wt. %, in relation to the total weight of the preparation (A); and
   m-aminophenol in an amount of from about 1.5 to about 3.0 wt. %, in relation to the total weight of the preparation (A).

8. The cosmetic product according to claim 1, wherein the preparation (B) comprises the percarbamide, percarbonate and/or perborate in a total amount of from about 25 to about 55 wt. %, in relation to the total weight of preparation (B).

9. The cosmetic product according to claim 1, wherein the water-soluble film, in relation to its total weight, comprises to an extent of at least 60 wt. % of a polymer mixture having a multimodal molecular weight distribution.

10. The cosmetic product according to claim 9, wherein the water-soluble film, in relation to its total weight, comprises to an extent of at least 60 wt. % of a polymer mixture having a bimodal molecular weight distribution.

11. The cosmetic product according to claim 9, wherein the polymer mixture, in relation to its total weight, consists to an extent of at least 60 wt. % of a mixture comprising:
   a1) water-soluble vinyl alcohol/vinyl acetate copolymer; and
   a2) at least one water-soluble vinyl alcohol/vinyl acetate copolymer different from the water-soluble vinyl alcohol/vinyl acetate copolymer a1); or of a mixture comprising:
   a1) water-soluble vinyl alcohol/vinyl acetate copolymer; and
   a2) at least one water-soluble polysaccharide.

12. The cosmetic product of claim 11 wherein the at least one water-soluble polysaccharide is selected from methylcellulose, carboxymethylcellulose, ethyl cellulose, hydroxyethyl cellulose, hydroxypropyl cellulose, hydroxypropyl methylcellulose, dextrin and hydroxypropyl starch.

13. The cosmetic product of claim 12 wherein the at least one water-soluble polysaccharide is a hydroxypropyl starch.

14. The cosmetic product of claim 11 wherein the polymer mixture, in relation to its total weight, consists to an extent of at least 80 wt. % of the mixture.

15. The cosmetic product of claim 11 wherein the polymer mixture, in relation to its total weight, consists to an extent of at least 90 wt. % of the mixture.

16. The cosmetic product according to claim 1, wherein the ratio by weight of the preparation (A) to the preparation (B) is from about 10:1 to about 1:10.

17. The cosmetic product according to claim 1, wherein the ratio by weight of the preparation (A) to the preparation (B) is from about 5:1 to about 1:5.

18. The cosmetic product according to claim 1, wherein the ratio by weight of the preparation (A) to the preparation (B) is from about 3:1 to about 1:3.

19. A method for dyeing keratin fibers comprising:
   preparing a preparation (A) comprising, based on its total weight, (a) at least one colorant from the group of oxidation dye precursors and substantive dyes, and (b) hydrated sodium silicate in an amount of from about 20 to about 80 wt. %;
   preparing a preparation (B) comprising, based on its total weight, at least one member from the group of percarbamide, percarbonates and perborates, in a total amount of from about 0.5 to about 95 wt. %;
   packaging the preparations (A) and (B) separately from one another in a water-soluble film as a cosmetic agent;
   adding the cosmetic agent to water in order to dissolve the water-soluble film, wherein the volume ratio of the totality of the preparations (A) and (B) to the water is from about 1:2 to about 1:8, to form an application mixture; and
   treating the keratin fibers with the application mixture.

20. The method of claim 19 wherein the volume ratio of the totality of the preparations (A) and (B) to the water is from about 1:2 to about 1:3.

* * * * *